United States Patent [19]

Esders et al.

[11] 4,042,461
[45] Aug. 16, 1977

[54] METHOD FOR PURIFYING CHOLESTEROL ESTERASE

[75] Inventors: Theodore Walter Esders, Webster; James Robert Schaeffer, Penfield; Harry Wayne Harris, Hamlin, all of N.Y.

[73] Assignee: Eastman Kodak Company, Rochester, N.Y.

[21] Appl. No.: 722,231

[22] Filed: Sept. 10, 1976

[51] Int. Cl.² .......................................... C07G 7/028
[52] U.S. Cl. ................................................ 195/66 R
[58] Field of Search ..................................... 195/66 R

[56] References Cited

FOREIGN PATENT DOCUMENTS 1,429,526  3/1976  United Kingdom

OTHER PUBLICATIONS

Kosugi et al., Journal of Fermentation Technology vol. 52, No. 8 pp. 577–582 (1974).

*Primary Examiner*—Lionel M. Shapiro
*Attorney, Agent, or Firm*—George W. Neuner

[57] ABSTRACT

Cholesterol esterase is purified by removal of the separable lipase in an enzyme preparation containing both cholesterol esterase and lipase activities by treatment using a hydrophobic chromatography column comprising carboxylated polysaccharide material having lower alkylamine with less than 8 carbon atoms attached thereto.

10 Claims, 2 Drawing Figures

METHOD FOR PURIFYING CHOLESTEROL ESTERASE

FIELD OF THE INVENTION

This invention is related to the field of enzyme purification and particularly to the purification of enzyme preparations having lipase and cholesterol esterase activities.

BACKGROUND OF THE INVENTION

In the quantitative determination of total cholesterol, it is necessary to convert the cholesterol esters into free cholesterol. This conversion can be accomplished chemically by alkaline hydrolysis or enzymatically using cholesterol esterase as described in British patent specification No. 1,429,526.

British patent specification No. 1,429,526 suggests that a preferred cholesterol esterase for this purpose is that found in enzyme preparations obtained by growing *Candida rugosa*. Other useful sources for cholesterol esterases described in this British Patent include: *Actinomyces aurcoverticillium* WS 90002, *Actinomyces cyaneofuscatus* WS 90003, *Actinomyces griseomycini* WS 90004, *Actinomyces longisporus-fl.* WS 90005, *Actinomyces malachiticus* WS 90006, *Actinomyces roseolus* WS 90007, *Actinomyces toxytricini* WS 90008, *Actinomyces variabilis Streptomyces spec.* WS 90010, *Streptomyces autotrophicus* WS 90011, *Streptomyces canescens* WS 90012, *Streptomyces chartreusis* WS 90013, *Streptomyces michiganensis* WS 90014, *Streptomyces murinus* WS 90015, *Streptomyces hachijoensis* WS 90016, *Streptomyces caelestes* WS 90017, *Streptomyces tendac* WS 90018, *Nocardia rubra* WS 90019, *Candida mycoderma* WS 90020, *Candida albicans* WS 90021, *Candida albicans* WS 90022, *Candida albicans* WS 90023, *Candida spec.* WS 90024, *Cunninghamella elegans* WS 90025, *Mucor muccdo* WS 90026, *Rhizopus spec.* WS 90027, *Penicillium spec.* WS 90028 and *Aspergillus spec.* WS 90029.

British patent specification No. 1,429,526 states that most microbial cholesterol esterases, such as those from the microorganisms listed above, are bound in lipoid membranes and are difficult to purify. The enzyme preparation obtained from *Candida rugosa* generally has large amounts of lipase activity associated with its cholesterol esterase activity. A method for purifying enzyme preparations suggested by British patent specification No. 1,429,526 to achieve up to a 20 to 30 fold enrichment of cholesterol esterase involves dialysis with a weakly basic anion exchange and an ammonium sulfate fractionation. Such methods have not been successful in separating the lipase activity from the cholesterol esterase activity of enzyme preparations such as that obtained from *Candida rugosa*.

A dry multilayer element for the quantitative analysis of analytes such as total cholesterol has been proposed by Goodhue et al in French Pat. No. 2,266,170, published Oct. 24, 1975. When making such elements it is desirable to reduce the amount of unnecessary solids such as extraneous proteins in the coatings in order to produce stable uniform coatings. Thus, when using an enzyme preparation from *Candida rugosa*, for example, for its cholesterol esterase (i.e., ester hydrolase) activity, it is desirable to reduce the substantial amounts of unwanted and unnecessary lipase activity and the protein associated therewith. The lipase activity may also affect the stability of the interactive materials present in the element and the precision of the analysis. The present invention provides a method for substantially removing the separable lipase activity from the desired cholesterol esterase activity in an enzyme preparation having separable lipase and cholesterol esterase activities.

SUMMARY OF THE INVENTION

In accord with the present invention, an enzyme preparation having separable lipase and cholesterol esterase activities is contacted with a hydrophobic chromatography column. The lipase and cholesterol esterase adhere to the column and the cholesterol esterase is eluted separately from the hydrophobic chromatography column using a stepwise salt gradient as described hereinafter. The column material comprises carboxylated polysaccharide material having attached thereto lower alkylamine with less than 8 carbon atoms. As used herein the term "carboxylated polysaccharide material" means a polysaccharide material having free carboxyl groups.

DETAILED DESCRIPTION OF THE INVENTION

Figure 1:
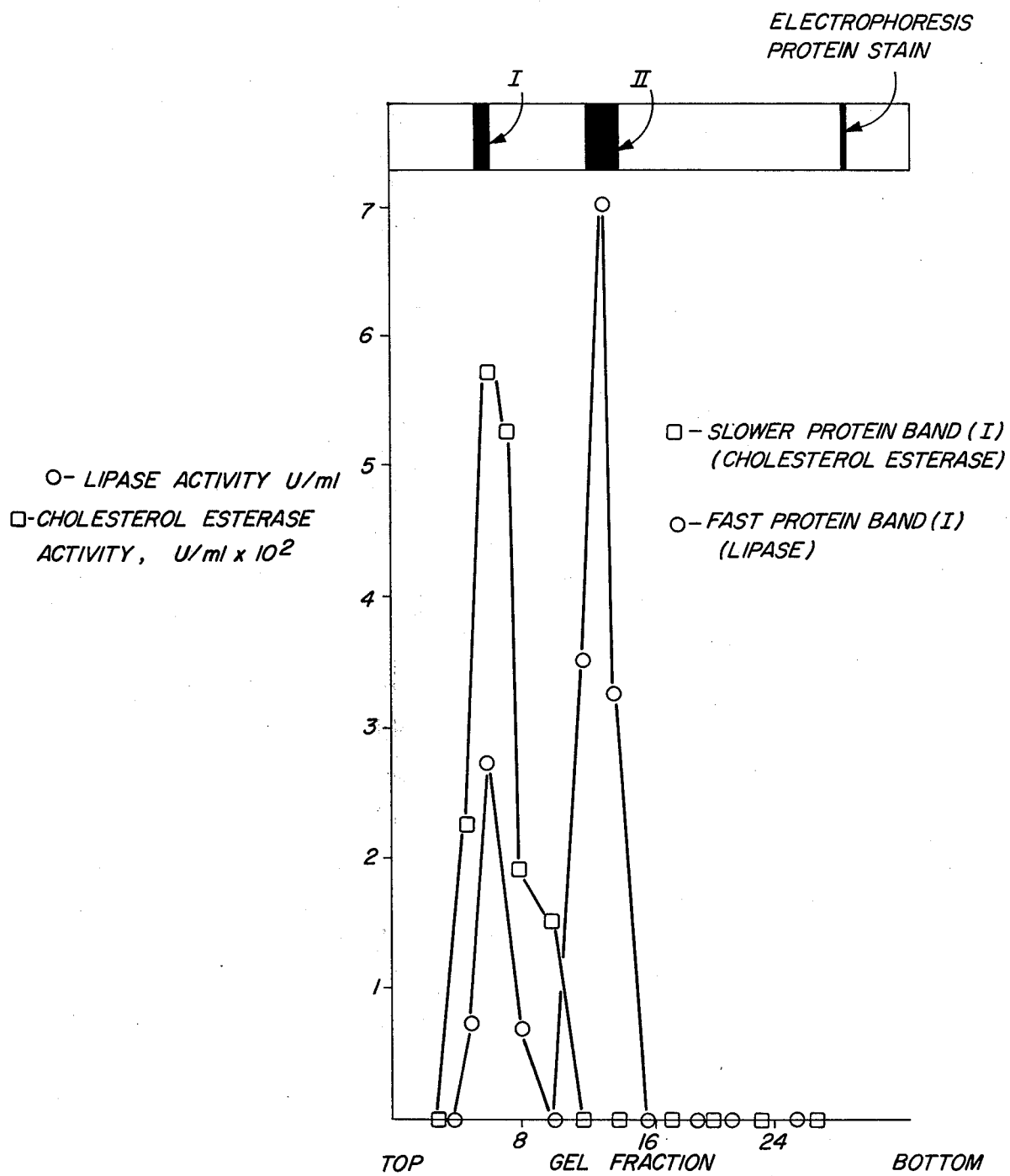
FIG. 1 is a graph showing the relative concentrations of cholesterol esterase activity and of lipase activity obtained by gel electrophoresis of a purified commercially available lipase preparation.

This invention provides a method for removing separable lipase activity from cholesterol esterase activity in an enzyme preparation having separable lipase and cholesterol esterase activities. The purification of various lipase preparations including that from *Candida rugosa* by affinity chromatography is described by Kosugi et al in "Affinity Chromatographic Studies on the Adsorption of Lipase on Aliphaticamine-Sepharose 4B", *Journal of Fermentation Technology*, Vol. 52, No. 8, pp. 577–82 (1974). Kosugi et al report that lipase can be purified by treatment on aliphaticamine-Sepharose 4B columns having aliphaticamines with 8 or more carbon atoms. The authors report that no purification was obtained using aliphaticamines with less than 8 carbon atoms. Apparently no recognition of the presence of cholesterol esterase activity was made and no mention is made of the separation of cholesterol esterase activity.

We have found that hydrophobic chromatography columns containing carboxylated polysaccharide material having attached thereto alkylamines with 8 or more carbon atoms are useful for purifying cholesterol esterase, including the cholesterol esterase from *Candida rugosa*. Alkylamine-carboxylated polysaccharide columns having alkylamines with 8 or more carbon atoms are not however useful to achieve separation of lipase activity from cholesterol esterase activity.

Electrophoresis of a commercially available lipase preparation from *Candida rugosa* (specifically Lipase M available from Enzyme Development Corp.) shows that the lipase activity and cholesterol esterase activity of the enzyme preparation is centered in two principle protein fractions. As can be seen by reference to FIG. 1, one of the active protein fractions contains substantially all of the cholesterol esterase activity and part of the total lipase activity, and the other protein fraction contains the bulk of the lipase activity and very small amounts of cholesterol esterase activity. It was found that treatment of this enzyme preparation by hydrophobic chromatography using lower alkylamine-carboxylated polysaccharide material separated these two protein fractions essentially to the same degree as electrophoresis. Compare the graphic results shown in FIG. 2 with those of FIG. 1.

Lower alkylamines which are useful as ligands on the polysaccharide materials in the process of this invention are those alkylamines having less than 8 carbon atoms. After the enzyme preparation is applied to the alkylamine-polysaccharide column, the cholesterol esterase and the lipase are eluted separately using a stepwise salt gradient. An example of eluting with a stepwise salt gradient as illustrated by Example 2 below includes eluting the column successively with salt solutions containing the following salt concentrations: 0, 0.1M, 0.2M, 0.4M, and 1.0M. As can be seen by referring to FIG. 2, the protein fraction containing the cholesterol esterase activity is substantially eluted at a low salt concentration.

Carboxylated polysaccharide materials are conveniently made by the well known technique that consists of activating the polysaccharide using cyanogen bromide and coupling an amino compound containing a free carboxyl group thereto. Any free carboxyl-containing group that can be coupled to the activated polysaccharide is useful herein. Free carboxyl-containing groups are obtained, for example, by attaching an aminoalkanoic acid or the like to the activated polysaccharide. Aminoalkanoic acids useful in the practice of this invention include those having from about 4 to about 30 carbon atoms, for example, aminohexanoic acid and the like. Alkylamines can then be attached to the carboxylated polysaccharide by the well-known carbodiimide reaction, an example of which is described at 5 below.

(Sepharose 4B is an agarose material available from Pharmacia Fine Chemicals, Inc. CH-Sepharose 4B is a cyanogen bromide-activated Sepharose 4B material having 6-aminohexanoic acid groups attached thereto, also available from Pharmacia Fine Chemicals, Inc.)

In the examples, unless otherwise indicated, the following procedures apply:

1. Assay for Lipase:
   a. Preparation of Lipid Substrates
      1. Aqueous triglyceride emulsion was prepared by sonifying 70 mg of olive oil (triglycerides) into 20 ml of deionized water for 7 minutes in an ice bath using a Branson sonifier. The resulting milky white emulsion was stable for three days at room temperature.
      2. A Triton X-100/cholesterol linoleate solution was prepared by dissolving 300 mg cholesteryl linoleate in 10 ml of hot Triton X-100 and adding 90 ml of deionized water. The clear solution was stable at room temperature for several weeks.
   b. Measurement of Lipase Activity Lipase activity was determined in a continuous spectrophotometric assay based on quantitating the glycerol released by hydrolysis of a triglyceride substrate. Glycerol was determined by means of Worthington Triglyceride Reagent, which contained in a total volume of 1.0 ml of pH 7.0 buffer: 1.08 $\mu$moles adenosine-triphosphate (ATP), 0.29 $\mu$moles phosphoenolpyruvate (PEP), 0.26 $\mu$moles reduced nicotinamide adenine dinucleotide (NADH), 0.12 units glycerol kinase, 0.66 units pyruvate kinase, and 1.32 units lactate dehydrogenase. An aliquot of the lipase sample was added to this, and the cuvette was brought to equilibrium in a Beckman Model 25 Spectrophotometer at 30° C., 340 nm. A 20 $\mu$l aliquot of triglyceride substrate was added, and absorbance at 340 nm was monitored. Lipase activity was determined from the initial linear portion of the curve, with a molar extinction coefficient for NADH at 340 nm of 6.22 $\times$ 10$^3$. Lipase units were expressed as "$\mu$moles of glycerol released per minute".

2. Assay for Cholesterol Esterase

Cholesterol esterase incubation mixtures contained in a total volume of 8 ml: 0.24 $\mu$moles aminoantipyrene-HCl, 0.12 $\mu$moles of 1,7-dihydroxynaphthalene, 0.25% Triton X-100, 0.168 mg peroxidase (125 purpurogallin units/mg solid), 0.195 units cholesterol oxidase, 300 $\mu$moles potassium phosphate buffer, pH 7.0, and 2.7 $\mu$moles cholesteryl linoleate. After samples were allowed to equilibrate at 37° C for 5 minutes, reactions were initiated by esterase addition and the absorbance at 490 nm was measured at 5 minute intervals for 20 minutes. A control tube contained all components except the cholesterol esterase so that color formation was dependent upon the esterase. Initial rates were calculated from the linear portion of the curve and expressed as: 1 unit of cholesterol esterase equals the amount of enzyme required to hydrolyze 1 $\mu$mole of cholesterol ester in 1 minute.

3. Determination of Protein

Protein was determined using the method of Lowry et al, *Journal of Biological Chemistry*, Vol. 193, page 265 (1951), with bovine serum albumin as standard.

4. Electrophoresis of Enzyme Preparations

Samples of partially purified enzyme preparations were electrophoresed according to the method of Hedrick and Smith, *Archives of Biochemistry and Biophysics*, Vol. 126, page 155 (1968), in 7% polyacrylamide gels. A tris-asparagine buffer with a running pH of 8.5 was used. A constant current of 1.5 milliamps/tube was applied with a Canalco apparatus; electrophoresis was allowed to proceed for 1.5 hours at 4° C. One 4.7 cm gel was stained for protein with 0.5% Amido-Schwarz dye in 7% acetic acid; a duplicate gel was sliced into 29 equal slices (1.62 mm each). Each slice was eluted with 150 $\mu$l of 0.1 M potassium phosphate buffer, pH 7.0, and assayed for lipase activity and cholesterol esterase activity as described above.

5. Immobilization of Butylamine on CH-Sepharose 4B

To 80 ml of chloroform were added 0.6 g of butylamine, 120 ml of dioxane, 5.0 g of activated, washed CH-Sepharose 4B, a modified agarose material available commercially from Pharmacia Fine Chemicals, Inc., Piscataway, N.J., and 0.5 g of dicyclohexylcarbodiimide. The reaction mixture was stirred at 50 rpm for 1 hour at room temperature. Then an additional 0.58 g of dicyclohexylcarbodiimide, dissolved in 3 ml of dioxane, was added and the reaction mixture was stirred for 24 hours at room temperature. The product was collected by vacuum filtration and dried under reduced pressure. The yield of the coupling reaction can be shown (based on 40 to 64 $\mu$moles/g of functional groups in the original polymer) by a repeat of the above synthesis with C$^{14}$ butylamine. A coupling yield of at least 50 to 60% is desirable. Other alkylamines can be coupled to CH-Sepharose 4B by a procedure similar to that described above.

EXAMPLE 1

Lipase M, an enzyme preparation with cholesterol esterase and lipase activities from *Candida rugosa* commercially available from Enzyme Development Corp., 2 Penn Plaza, N.Y., N.Y., was partially purified by hydrophobic chromatography using a column material having octadecylamine attached to CH-Sepharose 4B. The partially purified enzyme preparation was then treated by disc gel electrophoresis at pH 8.5. Two principle protein bands were found as illustrated by FIG. 1. By assaying gel slices for activity, it was observed that lipase activity was present in both protein bands whereas only the slower moving protein was active against cholesterol esters. The assayed activity is also plotted in FIG. 1.

EXAMPLE 2

A sample of Lipase M preparation, as purchased, was centrifuged, extensively dialysed against deionized water and lyophilized to obtain a non-dialyzable supernatant fraction (NDS). 50 mg of the Lipase M (NDS) in 2 ml of buffered solution was applied to a 10 ml chromatography column containing butylamine-CH-Sepharose 4B material, prepared as described above, which had been equilibrated with 5 mM potassium phosphate buffer at a pH of 7. Elution was carried out using a stepwise KCl gradient (10 fractions having salt concentrations of from 0 to 0.1 M KCl were used as depicted by the bar graph in FIG. 2). Fractions 1–6 contained 20 ml each and fractions 7–10 contained 10 ml each. The fractions were assayed spectrophotometrically for lipase and cholesterol esterase activities and the results are plotted in FIG. 2.

Figure 2:
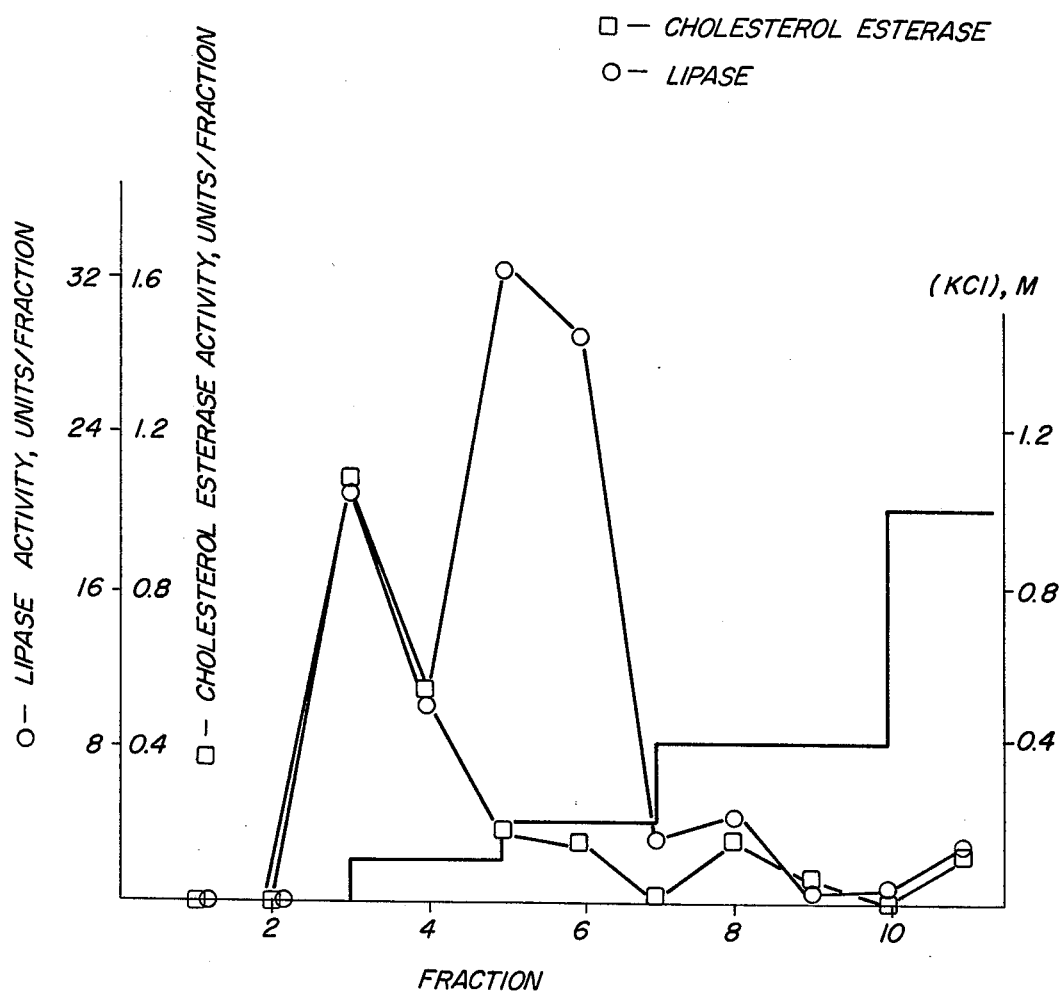
FIG. 2 is a graph showing the results obtained by treating a commercially available lipase preparation in accordance with the method described herein.

It can be noted by observing the results plotted in FIG. 2 and comparing them with FIG. 1, that the butylamine-CH-Sepharose 4B column substantially separated the cholesterol esterase activity from the separable lipase activity.

The results of two experiments to separate the separable lipase activity from the cholesterol esterase activity of a Lipase M preparation using a butylamine-CH-Sepharose 4B column are shown in Table I below. In the table, the specific activity of the NDS enzyme fraction prior to the chromatography step is reported as initial activity.

TABLE I

Recovery of Cholesterol Esterase and Lipase from a Butylamine-CH-Sepharose® 4B Column

| Enzyme Activity | Activity, Units | | Specific Activity, Units/mg | | |
|---|---|---|---|---|---|
| | Cholesterol Esterase Fraction | Lipase Fraction | Cholesterol Esterase Fraction | Lipase Fraction | Initial Activity |
| Experiment I | | | | | |
| Cholesterol Esterase | 1.11 | 0.33 | 0.32 | 0.14 | 0.12 |
| Lipase | 21 | 61 | 5.1 | 25 | 13 |
| Experiment II | | | | | |
| Cholesterol Esterase | 1.70 | 0.46 | 0.98 | 0.21 | 0.12 |
| Lipase | 5 | 95 | 1.3 | 53 | 13 |

It can be noted by observing the results shown in Table I that the specific activity of cholesterol esterase was increased 2.7–8.2 times by separation from the lipase activity.

The invention has been described in detail with specific reference to the preferred embodiments thereof, but it will be appreciated that modifications and extensions within the spirit and scope of this invention may be effected by those skilled in the art.

We claim:

1. A method for purifying a microbial enzyme preparation having separable cholesterol esterase and lipase activities, said method comprising:
   treating the enzyme preparation by hydrophobic chromatography using carboxylated polysaccharide material having attached thereto lower alkylamine with less than 8 carbon atoms to remove the separable lipase from the enzyme preparation to yield a purified cholesterol esterase preparation.

2. A method for purifying a microbial cholesterol esterase preparation having separable lipase activity, said method comprising:
   a. treating the cholesterol esterase preparation by hydrophobic chromatography using a column comprising carboxylated polysaccharide material having attached thereto lower alkylamine with less than 8 carbon atoms; and
   b. eluting cholesterol esterase separately from the separable lipase activity using a stepwise salt gradient.

3. The method as described in claim 2 wherein the carboxylated polysaccharide material is cyanogen bromide-activated agarose having a free carboxyl-containing group attached thereto.

4. The method as described in claim 2 wherein the carboxylated polysaccharide material comprises the reaction product of a cyanogen bromide-activated polysaccharide and an aminoalkanoic acid.

5. The method as described in claim 4 wherein the aminoalkanoic acid has from about 4 to about 30 carbon atoms.

6. The method as described in claim 4 wherein the aminoalkanoic acid is aminohexanoic acid.

7. The method as described in claim 2 wherein the alkylamine is butylamine.

8. A method for purifying a microbial cholesterol esterase preparation by removing separable lipase activity, said method comprising:
   a. applying the cholesterol esterase preparation to a hydrophobic chromatography column comprising a carbodiimide reaction product of (1) alkylamine having less than 8 carbon atoms and (2) cyanogen bromide-activated agarose having free carboxyl-containing group attached thereto; and
   b. eluting the cholesterol esterase with a stepwise salt gradient to remove separable lipase activity thereby obtaining a purified cholesterol esterase preparation.

9. The method as described in claim 8 wherein the alkylamine is butylamine and the aminoalkanoic acid has from about 4 to about 30 carbon atoms.

10. A method for removing separable lipase from an enzyme preparation having cholesterol esterase activity obtained by growing *Candida rugosa,* said method comprising:
    a. applying the enzyme preparation to a hydrophobic chromatography column comprising a reaction product of (1) butylamine and (2) cyanogen bromide-activated agarose having aminohexanoic acid attached thereto; and
    b. eluting the cholesterol esterase activity using a stepwise salt gradient to obtain a purified enzyme preparation having cholesterol esterase activity with separable lipase removed.

* * * * *